United States Patent
Jang et al.

(10) Patent No.: US 10,610,373 B2
(45) Date of Patent: Apr. 7, 2020

(54) SPINAL COMPLEX CAGE

(71) Applicant: MEDYSSEY CO., LTD., Jecheon-si, Chungcheongbuk-do (KR)

(72) Inventors: Jong-Wuk Jang, Seoul (KR); Ho-Jung Kim, Namyangju-si (KR); Kwun-Mook Lim, Jecheon-si (KR); Hyun-Woo Jung, Jecheon-si (KR); Jung-Hee Lee, Seoul (KR); In-Soo Oh, Seoul (KR); Jae-Young Hong, Uiwang-si (KR); Jae-Ho Yang, Paju-si (KR); Anthony Hunkyun Sin, Shreveport, LA (US)

(73) Assignee: MEDYSSEY CO., LTD., Jecheon-si (KR)

( * ) Notice: Subject to any disclaimer, the term of this patent is extended or adjusted under 35 U.S.C. 154(b) by 0 days.

(21) Appl. No.: 15/712,567

(22) Filed: Sep. 22, 2017

(65) Prior Publication Data

US 2018/0092754 A1    Apr. 5, 2018

(30) Foreign Application Priority Data

Oct. 4, 2016   (KR) .......................... 10-2016-0127696

(51) Int. Cl.
*A61F 2/44*    (2006.01)
*A61F 2/30*    (2006.01)
*A61F 2/46*    (2006.01)

(52) U.S. Cl.
CPC ........ *A61F 2/4455* (2013.01); *A61F 2/30744* (2013.01); *A61F 2/4611* (2013.01);
(Continued)

(58) Field of Classification Search
CPC ...................... A61F 2/44; A61F 2/4405; A61F 2/4455–447; A61F 2002/30604
See application file for complete search history.

(56) References Cited

U.S. PATENT DOCUMENTS

| 7,141,068 B2* | 11/2006 | Ross | ................... | A61F 2/30744 623/17.11 |
| 7,235,101 B2* | 6/2007 | Berry | ....................... | A61F 2/44 623/17.11 |

(Continued)

FOREIGN PATENT DOCUMENTS

KR    10-2008-0007113 A    1/2008
KR    10-2008-0093846 A    10/2008
(Continued)

OTHER PUBLICATIONS

An Office Action issued by the Korean Patent Office (KIPO) dated Sep. 25, 2017, which corresponds to Korean Patent Application No. 10-2016-0127696 and is related to U.S. Appl. No. 15/712,567; with English language translation.

*Primary Examiner* — Lynnsy M Summitt
(74) *Attorney, Agent, or Firm* — Studebaker & Brackett PC

(57) ABSTRACT

Disclosed is a spinal complex cage, which includes a cage which is made of a polymeric material, and metal covers which are formed on upper and lower portions of the cage, respectively, in which couplers formed on the metal covers are coupled to coupling grooves formed in the cage, such that the metal covers are detachably coupled to the upper and lower portions of the cage. Accordingly, because the cage and the metal cover are detachably coupled to each other, the manufacturing method is simple, and the metal cover is easily coupled to or separated from the cage, such that the spinal complex cage may be variously and quickly applied even during the surgery in accordance with shapes or intervals between the vertebral bodies, and as a result, a spinal fusion rate is excellent, and the accurate and precise surgical operation is enabled.

7 Claims, 16 Drawing Sheets

(52) U.S. Cl.
CPC .............. *A61F 2002/30003* (2013.01); *A61F 2002/305* (2013.01); *A61F 2002/30014* (2013.01); *A61F 2002/30028* (2013.01); *A61F 2002/30056* (2013.01); *A61F 2002/3092* (2013.01); *A61F 2002/30108* (2013.01); *A61F 2002/30316* (2013.01); *A61F 2002/30331* (2013.01); *A61F 2002/30387* (2013.01); *A61F 2002/30492* (2013.01); *A61F 2002/30507* (2013.01); *A61F 2002/30515* (2013.01); *A61F 2002/30599* (2013.01); *A61F 2002/30616* (2013.01); *A61F 2002/30784* (2013.01); *A61F 2002/30904* (2013.01); *A61F 2002/30909* (2013.01); *A61F 2002/30911* (2013.01); *A61F 2310/00023* (2013.01)

(56) References Cited

U.S. PATENT DOCUMENTS

| | | | |
|---|---|---|---|
| 7,250,060 B2 | 7/2007 | Trieu | |
| 7,285,134 B2* | 10/2007 | Berry | A61F 2/44 623/17.11 |
| 7,879,096 B2* | 2/2011 | Dickson | A61F 2/4611 606/90 |
| 8,268,002 B2 | 9/2012 | Blackwell et al. | |
| 8,303,879 B2* | 11/2012 | Bertele | A61F 2/30907 264/273 |
| 8,425,604 B2* | 4/2013 | Trieu | A61F 2/447 606/246 |
| 8,562,684 B2* | 10/2013 | Ullrich, Jr. | A61F 2/447 623/17.11 |
| 8,814,939 B2* | 8/2014 | Ullrich, Jr. | A61F 2/3094 623/17.11 |
| 9,125,756 B2* | 9/2015 | Ullrich, Jr. | A61F 2/4455 |
| 9,693,874 B2* | 7/2017 | Fang | A61F 2/4455 |
| 2003/0199980 A1* | 10/2003 | Siedler | A61F 2/44 623/17.11 |
| 2008/0154379 A1* | 6/2008 | Steiner | A61F 2/4455 623/17.16 |
| 2008/0161927 A1* | 7/2008 | Savage | A61F 2/4455 623/17.16 |
| 2008/0177387 A1* | 7/2008 | Parimore | A61F 2/30744 623/17.16 |
| 2011/0245927 A1* | 10/2011 | Farris | A61F 2/442 623/17.16 |
| 2012/0303127 A1* | 11/2012 | Ullrich, Jr. | A61F 2/4455 623/17.16 |
| 2013/0110248 A1* | 5/2013 | Zipnick | A61F 2/4455 623/17.16 |
| 2013/0166028 A1* | 6/2013 | Shieh | A61F 2/442 623/17.16 |
| 2016/0270931 A1* | 9/2016 | Trieu | A61F 2/30942 |

FOREIGN PATENT DOCUMENTS

| | | |
|---|---|---|
| KR | 10-2012-0119812 A | 10/2012 |
| KR | 10-2013-0090043 A | 8/2013 |
| KR | 10-1370424 B1 | 3/2014 |

\* cited by examiner

FIG. 3A
FIG. 3B
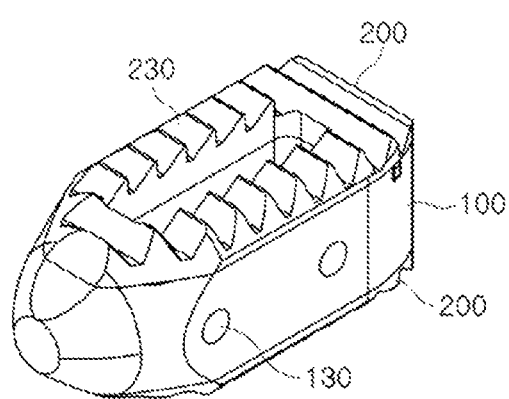
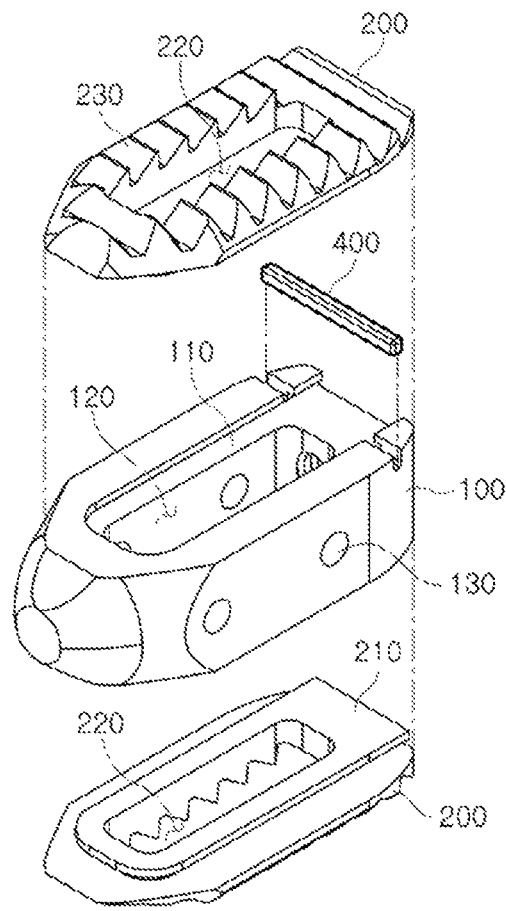

FIG. 4A
FIG. 4B
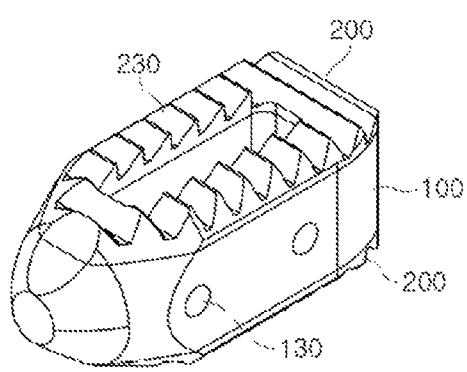
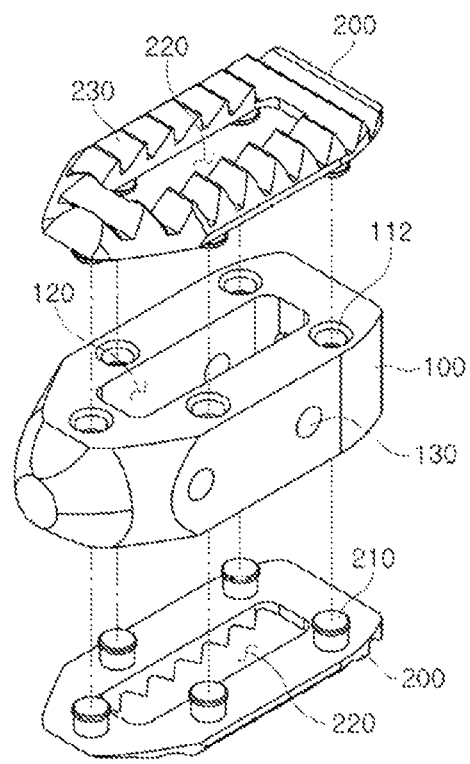

FIG. 5A
FIG. 5B
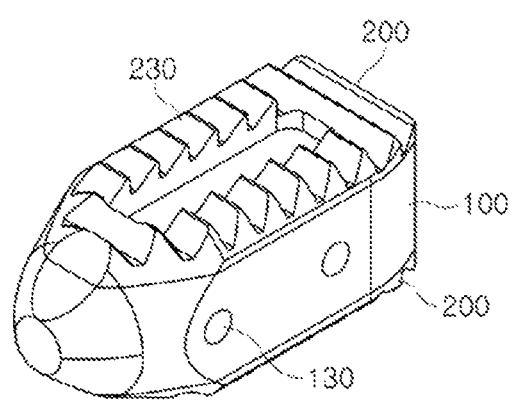
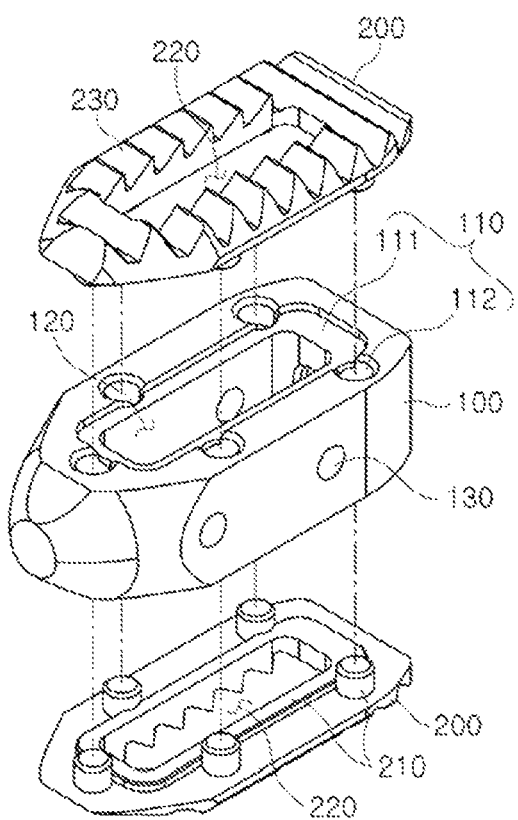

FIG.6A
FIG.6B
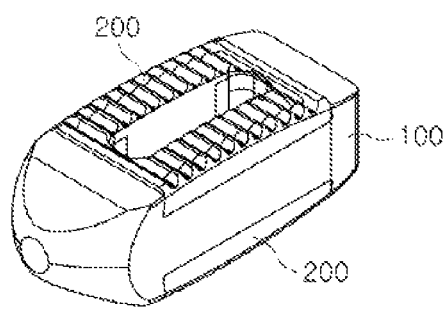
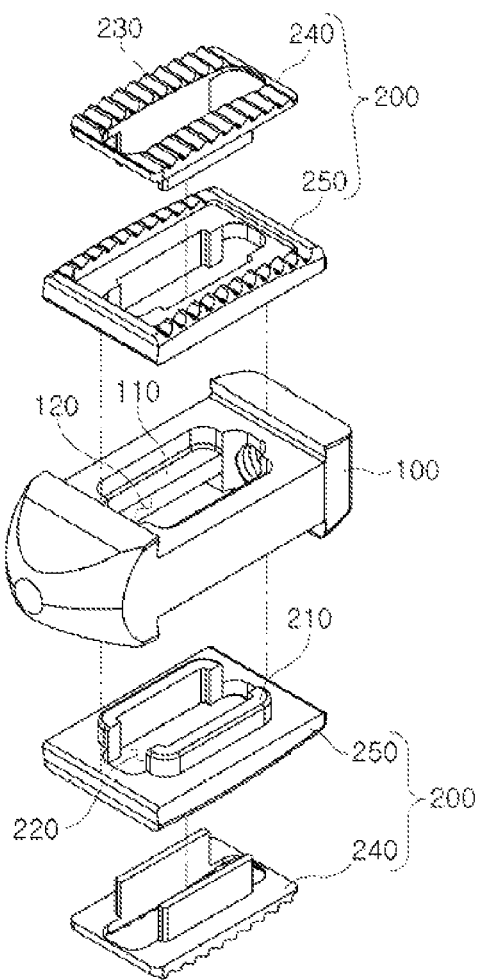

FIG. 8A
FIG. 8B
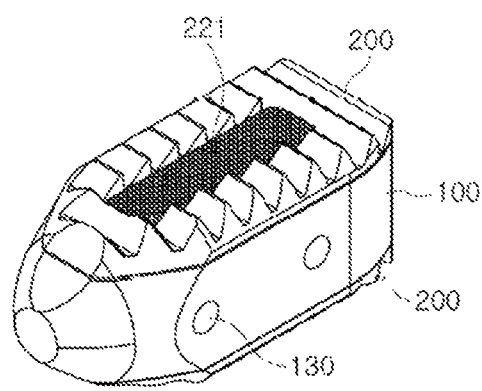
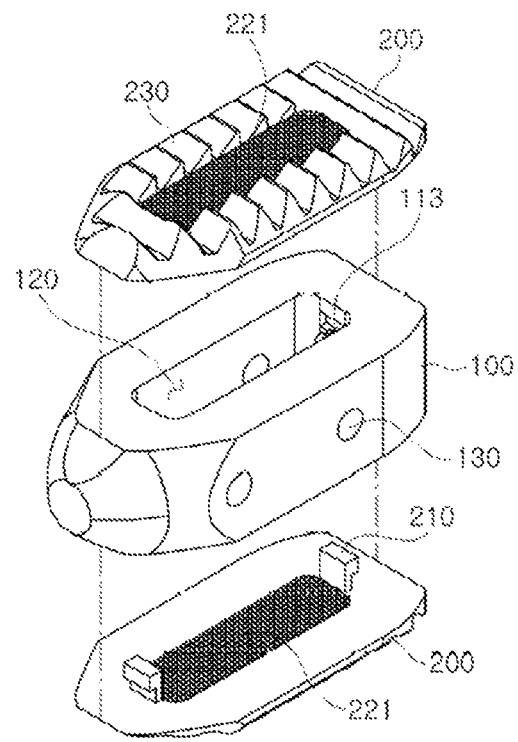

FIG. 9A
FIG. 9B
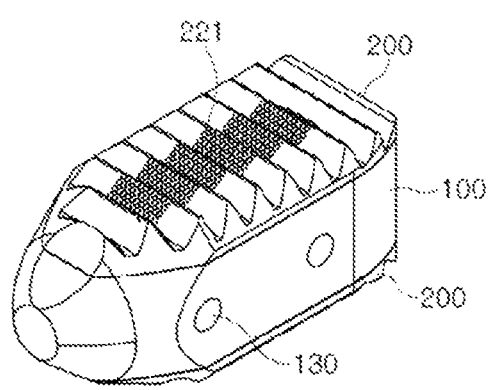
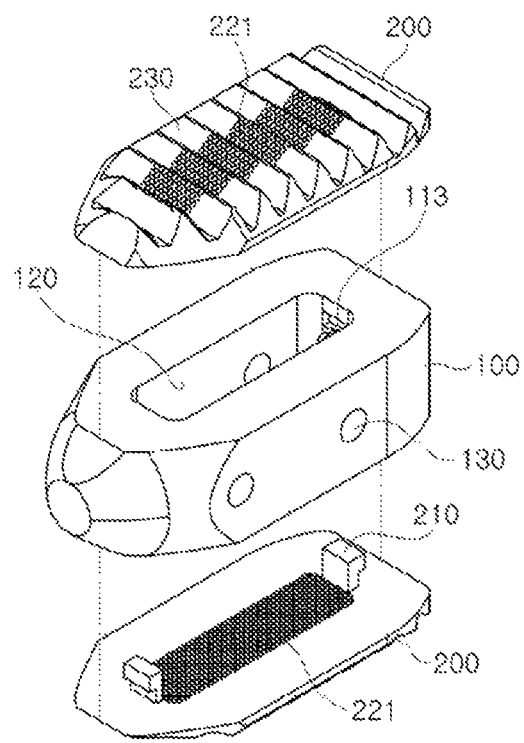

FIG. 10A
FIG. 10B
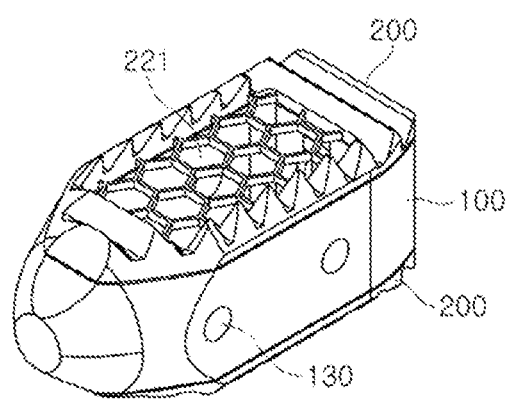
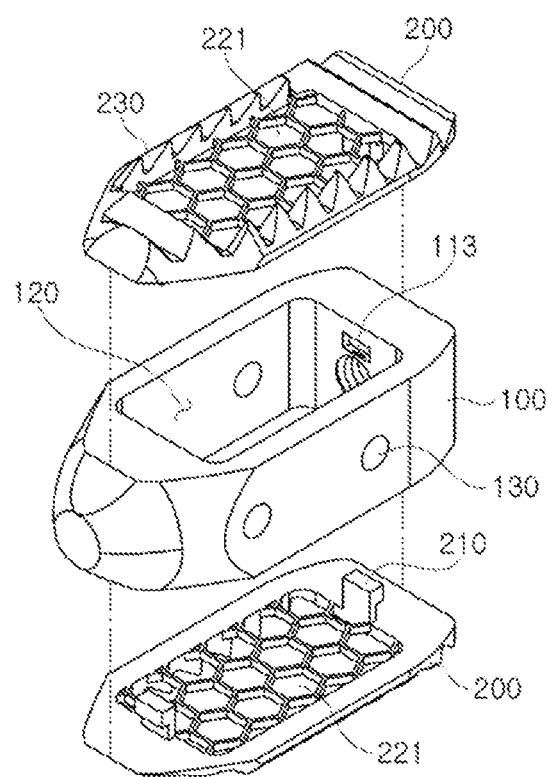

SPINAL COMPLEX CAGE

CROSS-REFERENCE TO RELATED APPLICATIONS

This application claims priority to and the benefit of Korean Patent Application No. 10-2016-0127696 filed in the Korean Intellectual Property Office on Oct. 4, 2016, the entire contents of which are incorporated herein by reference.

TECHNICAL FIELD

The present invention relates to a spinal complex cage and more particularly, to a spinal complex cage for an intervertebral body including a cage which is made of a polymeric material, and metal covers which are coupled to upper and lower portions of the cage, respectively, such that the spinal complex cage is made of a composite material containing polymers and metal for improving a spinal fusion rate.

BACKGROUND ART

In general, the vertebral column usually consists of 24 vertebrae (except for sacral vertebrae), and the vertebrae are connected through joints. Disks are placed between the joints for absorbing impacts and supporting loads when a human body moves or the joints move.

The vertebral column has an important function of not only supporting postures of the human body while absorbing impacts, but also protecting all organs in the body while supporting the motion of the human body.

However, if the vertebral column is injured or curved due to external and artificial causes, degenerative factors, or abnormal postures that continue for a long period of time, the vertebral column compresses the spinal cord passing through the spinal canal, which causes severe pain.

That is, a patient with the partially damaged vertebral column cannot perform activity required for personal life. Even in a case in which the vertebral column is not severely damaged, the damaged site of the vertebral column is pressed by or brought into contact with other adjacent parts, which causes pain.

A spinal complex cage, which is used for fusion which is one of the methods for surgically treating spinal diseases, is an implant that is implanted between upper and lower vertebral bodies after removing a damaged disc in order to assist bone grafting for lumbar vertebrae, treatments for spondylolisthesis, and fusion for spondylolisthesis and scoliosis. The spinal complex cage for an intervertebral body is used for a treatment of structural abnormalities such as degenerative lumbar herniated intervertebral discs, bone grafting for the vertebral column, fusion for spondylolisthesis and scoliosis, restoration of vertebral bodies in spondylolisthesis, restoration of heights of fractured vertebral bodies, and the like.

In the related art, the spinal complex cage for an intervertebral body is made of polyether ether ketone (PEEK). Because the PEEK material is a radiotransparent material, the spinal complex cage for an intervertebral body has been used while a titanium marker is inserted into a cage in order to ascertain a position of the cage in the computed tomography (CT).

However, the PEEK material is often damaged when the PEEK material is inserted between the vertebral bodies, and it is difficult to ascertain the exact position of the cage by means of the titanium marker.

The spinal complex cage for an intervertebral body made of titanium often deforms the vertebral bodies after surgery or causes subsidence into the vertebral bodies because of a high elastic modulus, which causes problems such as re-fracture or separation. Further, radiation cannot penetrate the spinal complex cage for an intervertebral body, which makes it difficult to determine spinal fusion in the CT.

To solve the aforementioned problems in the related art, Korean Patent No. 10-1370424 discloses a "spinal composite implant" which includes a cage which is made of resin, and a metal layer which is made of porous metal and attached to an outer surface of the cage.

The related art uses the resin cage and the metal layer and somewhat solves the aforementioned problems. However, the metal layer is attached to the resin cage by thermo-compression bonding, such that the manufacturing method is complicated. Further, because the spinal composite implant has a fixed size and a fixed shape, the spinal composite implant cannot be quickly applied in accordance with shapes and intervals between the vertebral bodies between which the spinal composite implant is to be inserted, which makes it difficult to accurately and precisely perform the surgical operation.

Because the metal layer is formed in a flat plate shape, the spinal composite implant cannot be securely fixed between the vertebral bodies, and there is a concern that the spinal composite implant is moved out of a position where the spinal composite implant is initially implanted, which causes deterioration in accuracy of the surgical operation.

DOCUMENT OF RELATED ART

Patent Document

Korean Patent Application Laid-Open No. 2008-0093846 (Artificial Disk for Anterior Lumbar Interbody Fusion)
Korean Patent No. 10-1370424 (Spinal Composite Implant)
U.S. Pat. No. 7,250,060 (Hybrid Intervertebral Disc System)

SUMMARY OF THE INVENTION

The present invention has been made in an effort to provide a spinal complex cage which includes a cage which is made of a polymeric material, and metal covers which are coupled to upper and lower portions of the cage, respectively, such that the spinal complex cage is made of a composite material containing polymers and metal.

An exemplary embodiment of the present invention provides a spinal complex cage, which includes a cage which is made of a polymeric material, and metal covers which are made of metal and formed on upper and lower portions of the cage, respectively, in which couplers formed on the metal covers are coupled to coupling grooves formed in the cage, such that the metal covers are detachably coupled to the upper and lower portions of the cage.

A front end portion of the cage may be formed in a streamlined shape, and the cage may have a hollow portion which vertically penetrates the cage, and a lateral hole portion which communicates with the hollow portion and horizontally penetrates the cage. A plurality of hollow portions of the cage may be arranged in a horizontal or vertical direction with respect to a direction in which the spinal complex cage is inserted between intervertebral bodies.

The metal cover may have an opening portion which communicates with the hollow portion. The opening portion may be formed in the form of a porous mesh for covering the hollow portion.

Spikes may be formed on an upper surface of the metal cover. The spike may be formed in the form of a triangular protrusion, and a surface of the spike, which is formed in the direction in which the spinal complex cage is inserted between the intervertebral bodies, is formed to have an angle smaller than 80° with respect to a lower surface of the metal cover.

The metal cover may be formed to have a porous structure.

The metal cover may include: an outer cover which is coupled to the cage and has a solid structure; and an inner cover which is accommodated in and coupled to the outer cover and has a porous structure.

The coupling grooves and the couplers may be formed such that the metal covers are fitted with the cage in a vertical direction. The coupling grooves may be configured as horizontal grooves which are horizontally formed in upper and lower surfaces of the cage so as to correspond to a shape of the hollow portion, or vertical grooves which are vertically formed in the upper and lower surfaces of the cage at the periphery of the hollow portion, or the coupling grooves may be configured as both of the horizontal grooves and the vertical grooves, and fitting grooves may be formed in a lateral direction so as to face an inner surface of the hollow portion of the cage.

The coupling grooves and the couplers may be formed such that the metal covers are slidably fitted with the cage in a lateral direction. The coupling grooves may be configured as a plurality of fitting grooves which is penetratively formed in upper and lower surfaces of the cage in the lateral direction.

The coupling grooves and the couplers may be formed such that the metal covers are slidably fitted with the cage from a rear side of the cage, and the cage and the metal covers may be fixed by means of coupling screws.

The coupling grooves and the couplers may be formed such that the metal covers are slidably fitted with the cage from a rear side of the cage, and a coupling bar may be further provided so that the metal covers are not withdrawn from the cage.

The coupling grooves may be formed in upper and lower surfaces of the cage so as to correspond to a shape of the hollow portion, and the coupling grooves may be horizontally formed to be opened at the rear side.

The cage may be inserted first between the vertebral bodies, and then the metal covers may be slidingly inserted, such that an interval between the vertebral bodies is expanded.

According to the present invention, it is possible to provide a spinal complex cage or a spinal complex cage for an intervertebral body, and more particularly, to a spinal complex cage including a cage which is made of a polymeric material, and metal covers which are formed on upper and lower portions of the cage, respectively, such that the spinal complex cage is made of a composite material containing polymers and metal.

Because the cage and the metal cover are detachably coupled to each other, the manufacturing method is simple, and the metal cover is easily coupled to or separated from the cage, such that the spinal complex cage may be variously and quickly applied even during the surgery in accordance with shapes or intervals between the vertebral bodies, thereby enabling the accurate and precise surgical operation.

The metal cover with the porous structure is applied to the portion which is in contact with the bone, and this configuration is advantageous to bone grafting. The cage made of a polymeric material may support lumbar vertebrae with appropriate strength, and the cage imparts elasticity most similar to that of the human bone, such that there is no adverse effect, and radiation transmittance is high. The metal cover serves as a marker in the radiograph, and as a result, it is possible to accurately ascertain whether spinal fusion is carried out, thereby increasing a success rate of the surgical operation.

BRIEF DESCRIPTION OF THE DRAWINGS

FIGS. 3A and 3B are views illustrating various exemplary embodiments of the present invention.

FIGS. 4A and 4B are views illustrating various exemplary embodiments of the present invention.

FIGS. 5A and 5B are views illustrating various exemplary embodiments of the present invention.

FIGS. 6A and 6B are views illustrating various exemplary embodiments of the present invention.

FIGS. 8A and 8B are views illustrating various exemplary embodiments of the present invention.

FIGS. 9A and 9B are views illustrating various exemplary embodiments of the present invention.

FIGS. 10A and 10B are views illustrating various exemplary embodiments of the present invention.

DETAILED DESCRIPTION

Figure 1A:
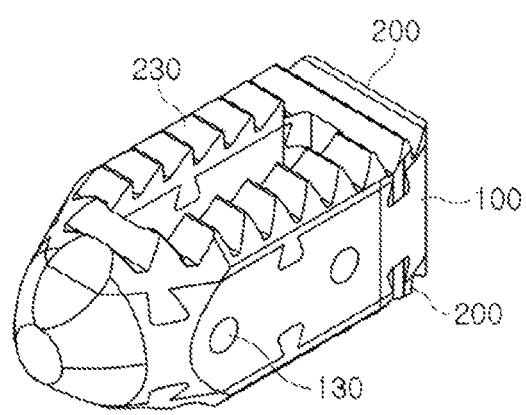
FIGS. 1A and 1B are views illustrating various exemplary embodiments of the present invention.
Figure 1B:
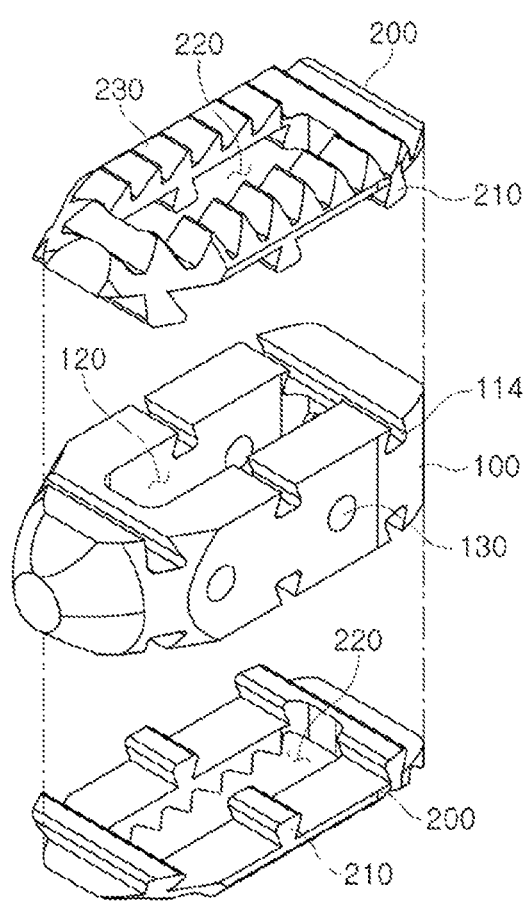
Figure 2A:
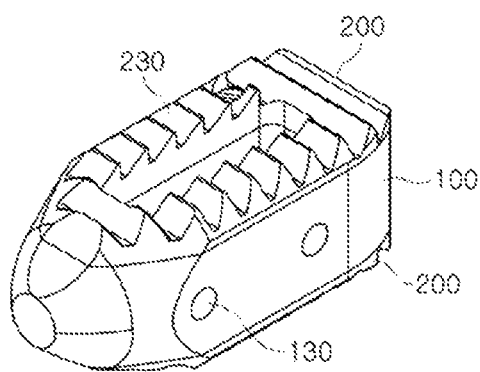
FIGS. 2A and 2B are views illustrating various exemplary embodiments of the present invention.
Figure 2B:
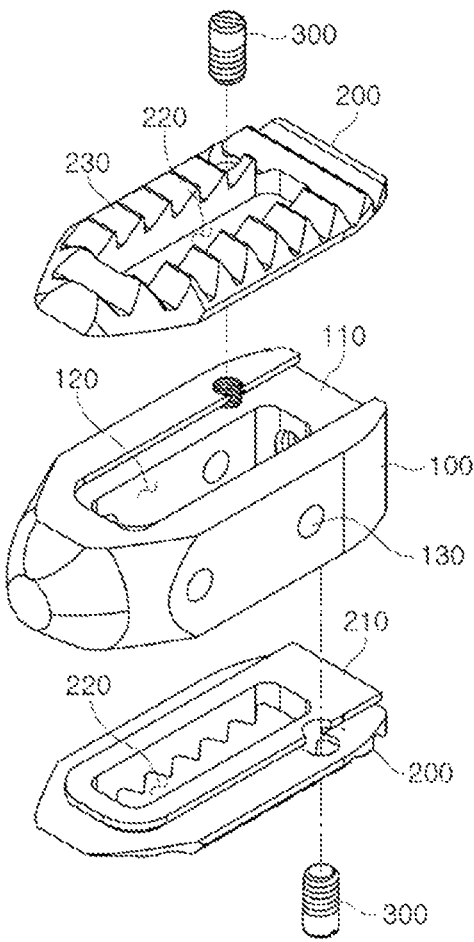
Figure 7A:
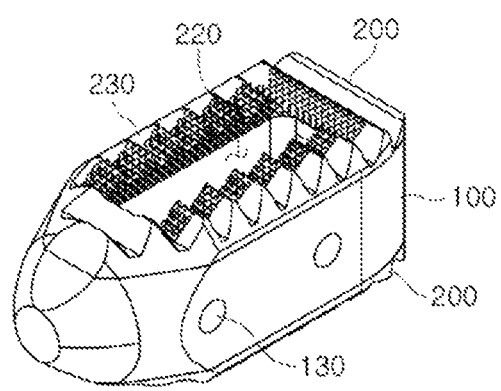
FIGS. 7A and 7B are views illustrating various exemplary embodiments of the present invention.
Figure 7B:
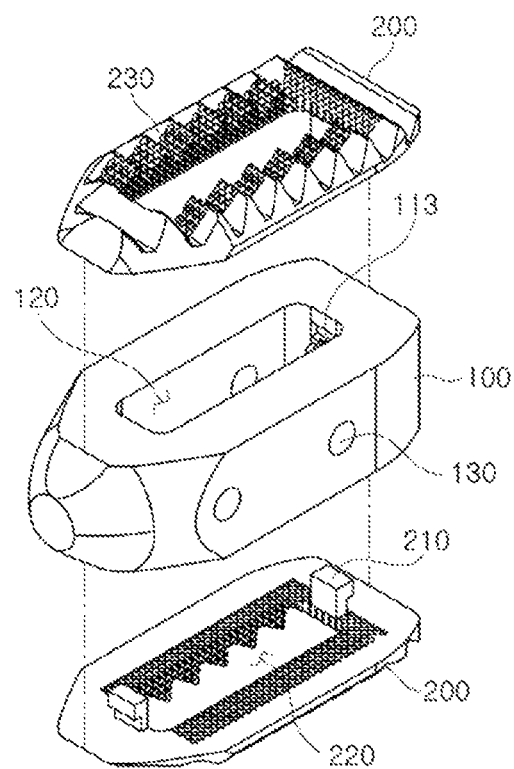

The present invention relates to a spinal complex cage, and more particularly, to a spinal complex cage for an intervertebral body including a cage which is made of a polymeric material, and metal covers which are formed on upper and lower portions of the cage, respectively, such that the spinal complex cage is made of a composite material containing polymers and metal.

In particular, because the cage and the metal covers are detachably coupled to each other, the manufacturing method is simple, and the metal cover is easily coupled to or separated from the cage, such that the spinal complex cage may be variously and quickly applied even during surgery in accordance with shapes or intervals between the vertebral bodies, thereby enabling the accurate and precise surgical operation.

Hereinafter, the present invention will be described with reference to the accompanying drawings. FIGS. 1 to 15 illustrate exemplary embodiments of the present invention, in which FIGS. 1A, 2A, 3A, 4A, 5A, 6A, 7A, 8A, 9A, and 10A are perspective views, and FIGS. 1B, 2B, 3B, 4B, 5B, 6B, 7B, 8B, 9B, and 10B are exploded perspective views, and FIG. 16 is a view illustrating a state in which the exemplary embodiment of the present invention is used.

As illustrated in the drawings, the present invention provides a spinal complex cage for an intervertebral body which includes a cage 100 which is made of a polymeric material, and metal covers 200 which are made of metal and formed on upper and lower portions of the cage 100, respectively, and is characterized in that a coupler 210 formed on the metal cover 200 is coupled to a coupling groove 110 formed in the cage 100, such that the metal covers 200 are detachably coupled to the upper and lower portions of the cage 100.

The spinal complex cage according to the present invention includes the cage 100 made of a polymeric material, and the metal cover 200 made of metal, thereby complementarily coping with the defects of the polymeric material and the metal.

As the polymeric material, polyether ether ketone (PEEK) having excellent biocompatibility is used, or carbon-PEEK or ultra-high molecular weight polyethylene (UHMWPE) may be used. As the metal, a titanium alloy having excellent biocompatibility is used, or stainless steel, nitinol, or a cobalt-chromium alloy (Co—Cr alloy) may be used.

The PEEK has mechanical strength which is suitable to support the vertebral column in the body but lower than titanium, and the PEEK has excellent biocompatibility, such that the PEEK is widely used as a material of the cage 100. The PEEK has an elastic modulus similar to the human's bone, thereby preventing a stress shielding effect. Because radiation can penetrate the PEEK, it is possible to recognize a process of spinal fusion and a process of creating bones which are performed in the PEEK cage 100. However, the PEEK has a defect in that a spinal fusion rate is low after surgery and a fusion period is slightly long.

Titanium has excellent mechanical strength suitable to support the vertebral column in the body, and has excellent biocompatibility, but titanium has a much larger elastic modulus than the ossein of the human body, which increases a likelihood of the occurrence of adverse effects such as subsidence in the bone. The radiation does not penetrate titanium, which makes it difficult to ascertain a therapeutic effect such as spinal fusion. However, since titanium has excellent biocompatibility, a spinal fusion rate is increased, such that a patient can be quickly recovered.

As described above, the present invention relates to a spinal complex cage in which the metal covers 200 are coupled to the upper and lower portions of the PEEK cage 100, thereby complementarily coping with the advantages and the disadvantages of the materials.

That is, the upper and lower parts, which are in contact with the bone, are made of titanium with a high spinal fusion rate, particularly, embodied to have spikes 230 made of a porous material in order to ensure quick fusion with the bone. Further, the cage 100 is made of the PEEK which has a similar strength to the human's sternum, such that the cage 100 has high biocompatibility. Therefore, only the advantages of the two materials, such as prevention of subsidence and improvement of therapeutic effects by using radiation penetration, are combined.

For example, a titanium material with a porous structure is applied to a portion which is in contact with the bone, and this configuration is advantageous to frictional force and bone grafting. The cage made of PEEK may support lumbar vertebrae with appropriate strength, and the PEEK has excellent biocompatibility, such that the cage 100 made of PEEK imparts elasticity most similar to that of the human's bone. Therefore, the cage 100 made of PEEK has an elastic modulus similar to that of the human's bone, and has high radiation transmittance. The titanium serves as a marker in a radiograph, thereby making it possible to accurately ascertain whether spinal fusion is carried out. There is provided a porous structure in which the portion, which is in direct contact with the bone, is made of titanium having the highest spinal fusion rate in order to ensure fusion with the bone.

As described above, it is possible to provide an optimized implant to a patient by supplementing the defects of the materials and maximizing the advantages of the materials. The porous titanium structure, which is used for a portion being in direct contact with the bone, allows blood and organic substances to more easily flow compared to a structure which is formed in the form of a solid, such that the porous titanium structure is effective in increasing the spinal fusion rate. The porous titanium structure is very advantageous in terms of the therapeutic effect for the patient, and increases a success rate of a surgical operation by inducing a high spinal fusion rate after surgery.

Because of the radiation transmittance properties of the PEEK, it is possible to recognize a process of spinal fusion of grafted bone inserted into the cage and a process of creating bones after surgery. The cover made of titanium often deforms the vertebral body or causes subsidence into the vertebral bodies after surgery because of a high elastic modulus, but the cage made of PEEK is used to impart elasticity similar to that of the human bone, thereby reducing an adverse effect such as a reoperation caused by subsidence after surgery.

The metal cover or porous metal cover may be produced by using metal powder and a metal 3D printer, such that the metal cover or porous metal cover may be easily and precisely produced.

As described above, in the spinal complex cage made of the polymer and the metal, the coupler 210 formed on the metal cover 200 is coupled to the coupling groove 110 formed in the cage 100, and the metal covers 200 are detachably coupled to the upper and lower portions of the cage 100, respectively.

The coupling groove 110 formed in the cage 100 and the coupler 210 formed on the metal cover 200 are formed to face each other and detachably coupled to each other, such that the spinal complex cage is made of a composite material through a simple method. The metal cover 200 is easily separated from and coupled to the cage 100, such that the spinal complex cage may be quickly embodied in various forms in accordance with shapes and intervals between the vertebral bodies even during surgery, thereby enabling an accurate and precise surgical operation.

A front end portion of the cage 100 is formed in a streamlined shape, and the cage 100 has a hollow portion 120 which vertically penetrates the cage 100, and lateral hole portions 130 which communicate with the hollow portion 120 and horizontally penetrate the cage 100.

Since the front end portion of the cage 100 is formed in a streamline shape, that is, the front end portion of the cage 100 is formed to have a small cross-sectional area, such that the cage 100 is easily inserted between the intervertebral bodies. The hollow portion 120 is filled with bone chips or bone cement such as artificial bone or autogenous bone, and the fusion is carried out by bone growth from the adjacent vertebral bodies through the hollow portion 120 or the lateral hole portions 130.

A plurality of hollow portions 120 of the cage may be arranged in a horizontal or vertical direction with respect to a direction in which the spinal complex cage is inserted between the vertebral bodies. The plurality of hollow portions 120 may be formed in consideration of a spinal fusion rate and rigidity in accordance with shapes of the vertebral body and lesions, and the hollow portion 120 may be formed in various shapes such as a curved surface shape.

The metal cover 200 has an opening portion 220 that communicates with the hollow portion 120, and a bone grafting material accommodated in the hollow portion 120 is exposed through the opening portion 220, such that the spinal fusion is carried out by the bone growth from the adjacent vertebral bodies.

The opening portion 220 may be formed in the form of a porous mesh 221 that covers the hollow portion 120. The opening portion maintains the spinal fusion rate to a predetermined degree while preventing a loss of the bone grafting material accommodated in the hollow portion 120 when the opening portion is initially fixed.

The spikes 230 are formed on an upper surface of the metal cover 200. The spike 230 is formed in the form of a triangular protrusion, and a surface of the spike 230, which is formed in the direction in which the spinal complex cage is inserted between the vertebral bodies, is formed to have an angle smaller than 80° with respect to a lower surface of the metal cover 200, such that the spinal complex cage is easily inserted between the vertebral bodies, but rarely withdrawn in the direction in which the spinal complex cage is inserted.

The metal cover 200 has a porous structure as described above, and the porous structure is used for a portion which is in direct contact with the bone. Therefore, blood and organic substances more easily flow and a spinal fusion rate is increased, which advantageously improves the therapeutic effect for the patient, and a high spinal fusion rate is induced after surgery to increase a success rate of the surgical operation.

A size of a pore of the metal cover 200 having the porous structure is about 450 to 700 µm. In the metal cover 200 in the form of the porous mesh 221 for covering the hollow portion 120, a thickness of a mesh column is about 300 to 800 µm, and the porosity is 87.4%. The size of the pore, the size of the mesh, and the porosity are designed in consideration of the spinal fusion rate and rigidity of the metal cover 200.

Here, the metal cover 200 may include an outer cover 240 which is coupled to the cage 100 and has a solid structure, and an inner cover 250 which is accommodated into and coupled to the outer cover 240 and has a porous structure. With this configuration, the spinal fusion rate and the rigidity of the metal cover 200 are maintained.

Meanwhile, according to the present invention, the coupling groove 110 formed in the cage 100 and the coupler 210 formed in the metal cover 200 are formed to face each other so that the coupling groove 110 formed in the cage 100 and the coupler 210 formed in the metal cover 200 may be fitted with and coupled to each other.

The coupling grooves 110 and the couplers 210 are formed such that the metal covers 200 may be fitted with the cage 100 in a vertical direction. In this case, the coupling grooves 110 may include horizontal grooves 111 which are horizontally formed in upper and lower surfaces of the cage 100 so as to correspond to a shape of the hollow portion 120, or vertical grooves 112 which are vertically formed in the upper and lower surfaces of the cage 100 at the periphery of the hollow portion 120. The coupling grooves 110 may include both of the horizontal grooves 111 and the vertical grooves 112, or fitting grooves 113 may be formed in a lateral direction so as to face the inner surface of the hollow portion 120 of the cage 100.

The coupling grooves 110 and the couplers 210 are formed such that the metal covers 200 are slidably fitted with the cage 100 in the lateral direction. In this case, the coupling grooves 110 are configured as a plurality of fitting grooves 114 which is penetratively formed in the upper and lower surfaces of the cage 100 in the lateral direction.

The coupling grooves 110 and the couplers 210 may be formed such that the metal covers 200 are slidably fitted with the cage 100 from a rear side of the cage 100, and the cage 100 and the metal covers 200 may be fixed by means of coupling screws 300.

The coupling grooves 110 and the couplers 210 may be formed such that the metal covers 200 are slidably fitted with the cage 100 from the rear side of the cage 100, and a coupling bar 400 may be further provided so that the metal cover 200 is not withdrawn from the cage 100. Here, the coupling grooves 110 may be horizontally formed in the upper and lower surfaces of the cage 100 so as to correspond to the shape of the hollow portion 120, and the coupling grooves 110 may be horizontally formed to be opened at the rear side.

Hereinafter, various exemplary embodiments of the present invention will be described in detail with reference to the accompanying drawings. FIGS. 1 to 11 illustrate various exemplary embodiments of the spinal complex cage according to the present invention.

First, FIG. 1 illustrates the spinal complex cage which includes the cage 100 which is made of PEEK, and the metal covers 200 which are made of titanium and formed on the upper and lower portions of the cage 100, respectively. The coupler 210 formed on the metal cover 200 is coupled to the coupling groove 110 formed in the cage 100, such that the metal covers 200 are detachably coupled to the upper and lower portions of the cage 100. A groove portion (screw thread) for coupling a cage insertion instrument is formed at a rear side of the spinal complex cage.

As illustrated in the drawings, the coupling grooves 110 and the couplers 210 are formed such that the metal covers 200 are slidably fitted with the cage 100 in the lateral direction. In this case, the coupling grooves 110 are configured as a plurality of fitting grooves 114 which is penetratively formed in the upper and lower surfaces of the cage 100 in the lateral direction.

The fitting grooves 114 and the couplers 210 are formed such that the metal covers 200 are slidably fitted with the cage 100 in the lateral direction of the cage 100, and catching projections may be formed at the end portion of the coupler 210 and the end portion of the fitting groove 114 so that the metal covers 200 may be separated from the cage 100 in the lateral direction, but the metal covers 200 cannot be separated in the vertical direction.

The cage 100 has the hollow portion 120 and the lateral hole portions 130. The metal cover 200 has the opening portion 220 that communicates with the hollow portion 120, and the spikes 230 are arranged on the upper surface of the metal cover 200 perpendicularly to the direction in which the spinal complex cage is inserted between the intervertebral bodies.

In FIG. 2, the coupling grooves 110 and the couplers 210 are formed such that the metal covers 200 are slidably fitted with the cage 100 from the rear side of the cage 100, and the cage 100 and the metal covers 200 are fixed by means of the coupling screws 300. The coupling grooves 110 are formed in the upper and lower surfaces of the cage 100 so as to correspond to the shape of the hollow portion 120, and the coupling grooves are horizontally formed to be opened at the rear side. The shape of the coupler 210 corresponds to the shape of the coupling groove.

In FIG. 3, the coupling grooves 110 and the couplers 210 are formed such that the metal covers 200 are slidably fitted with the cage 100 from the rear side of the cage 100, and the coupling bar 400 is further provided so that the metal cover 200 is not withdrawn from the cage 100. The coupling grooves 110 are formed in the upper and lower surfaces of the cage 100 so as to correspond to the shape of the hollow portion 120, and the coupling grooves 110 are horizontally formed to be opened at the rear side. The shape of the coupler 210 corresponds to the shape of the coupling groove.

The coupling bar 400 is inserted into a recess formed in the cage 100. The metal cover 200 is slidably coupled, and then the coupling bar 400 is coupled, such the metal cover 200 is fixed and prevented from being withdrawn.

In FIG. 4, the coupling grooves 110 and the couplers 210 are formed such that the metal covers 200 are fitted with the cage 100 in the vertical direction. In this case, the coupling grooves 110 are configured as the vertical grooves 112 which are vertically formed in the upper and lower surfaces of the cage 100 at the periphery of the hollow portion 120.

A plurality of vertical grooves 112 is formed, and the couplers 210 are formed to correspond to the vertical grooves 112.

In FIG. 5, the coupling grooves 110 and the couplers 210 are formed such that the metal covers 200 are fitted with the cage 100 in the vertical direction. In this case, the coupling grooves 110 include both of the horizontal grooves 111 which are horizontally formed in the upper and lower surfaces of the cage 100 so as to correspond to the shape of the hollow portion 120, and the vertical grooves 112 which are vertically formed in the upper and lower surfaces of the cage 100 at the periphery of the hollow portion 120. The couplers 210 are formed to correspond to the coupling grooves 110.

In FIG. 6, the metal cover 200 includes the outer cover 240 which is coupled to the cage 100 and has a solid structure, and the inner cover 250 which is accommodated into and coupled to the outer cover 240 and has a porous structure.

In the present exemplary embodiment, the coupling grooves 110 and the couplers 210 are formed such that the metal covers 200 are fitted with the cage 100 in the vertical direction. The horizontal grooves 111 are horizontally formed in the upper and lower surfaces of the cage 100 so as to correspond to the shape of the hollow portion 120, and coupled to the couplers 210 of the metal covers 200 in an interference fit manner.

In FIGS. 7 to 10, the coupling grooves 110 and the couplers 210 are formed such that the metal covers 200 are fitted with the cage 100 in the vertical direction. The coupling grooves 110 are configured as the fitting grooves 113 which are formed in the lateral direction so as to face the inner surface of the hollow portion 120 of the cage 100.

In FIG. 7, the opening portion 220 is formed in the metal cover 200, and a porous structure is provided at the periphery of the opening portion 220.

In FIG. 8, the opening portion 220 of the metal cover 200 is formed in the form of the porous mesh 221 for covering the hollow portion 120, and the porous mesh 221 of the opening portion 220 is formed in a flat shape. In FIG. 9, the opening portion 220 of the metal cover 200 is formed in the form of the porous mesh 221 for covering the hollow portion 120, and the porous mesh 221 of the opening portion 220 is continuously formed on the spikes 230 of the metal cover 200.

Here, the porous structure and the porous mesh 221 are implemented in different forms from the porous structure and the porous mesh 221 formed in the opening portion 220 (in the form of the porous mesh 221), and there is no difference in terms of a manufacturing method and a size of the pore. Here, a difference in pore may vary in accordance with the spinal fusion rate or the rigidity of the metal cover 200.

In FIG. 10, the opening portion 220 of the metal cover 200 is formed in the form of the porous mesh 221 for covering the hollow portion 120. The porous mesh 221 of the opening portion 220 is formed in a flat shape, and the porous mesh 221 is formed in a honeycomb shape with pores having a relatively large size unlike the configuration illustrated in FIG. 8.

Figure 11A:
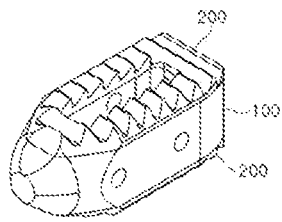
FIGS. 11A, 11B and 11C are views illustrating various exemplary embodiments of the present invention.
Figure 11B:
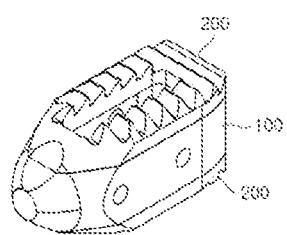
Figure 11C:
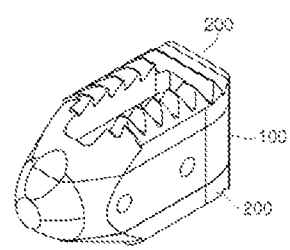
Figure 12A:
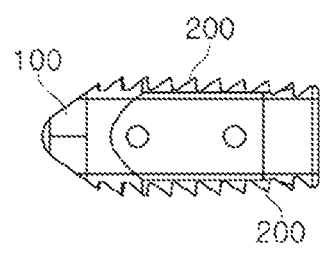
FIGS. 12A, 12B and 12C are views illustrating various exemplary embodiments of the present invention.
Figure 12B:
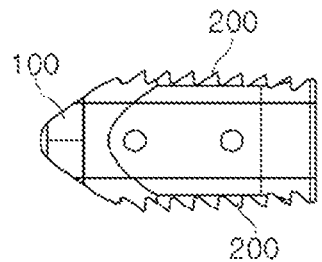
Figure 12C:
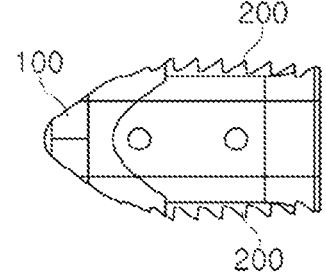

FIGS. 11A to 11C and 12A to 12C are views (in which FIGS. 11A to 11C are perspective views, and FIGS. 12A to 12C are schematic side view) illustrating the metal covers 200 which have different heights in the spinal complex cage according to the exemplary embodiment in FIG. 4 or 5. Since the metal covers 200 are easily separated from and coupled to the cage 100, an overall height of the spinal complex cage may be adjusted by quickly changing the metal covers 200 in accordance with shapes and intervals between the vertebral bodies during surgery in the operating room, such that the fusion prostheses with various sizes may be provided, thereby enabling an accurate and precise surgical operation.

Figure 13:
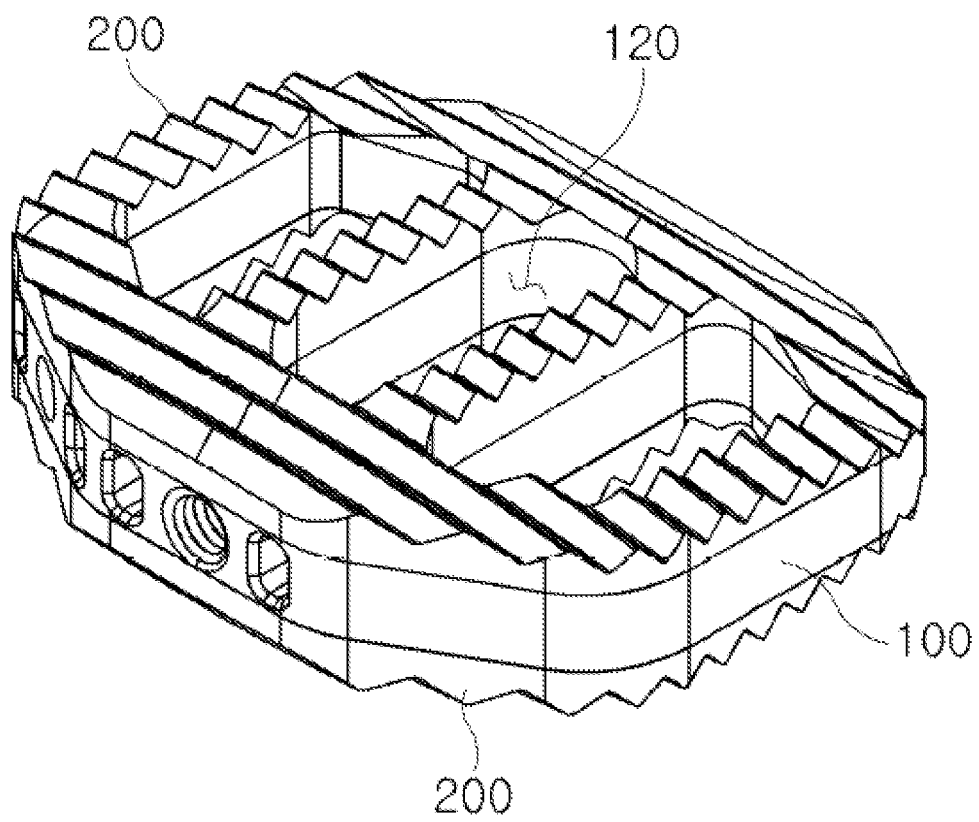
FIG. 13 is a view illustrating various exemplary embodiments of the present invention.
Figure 14:
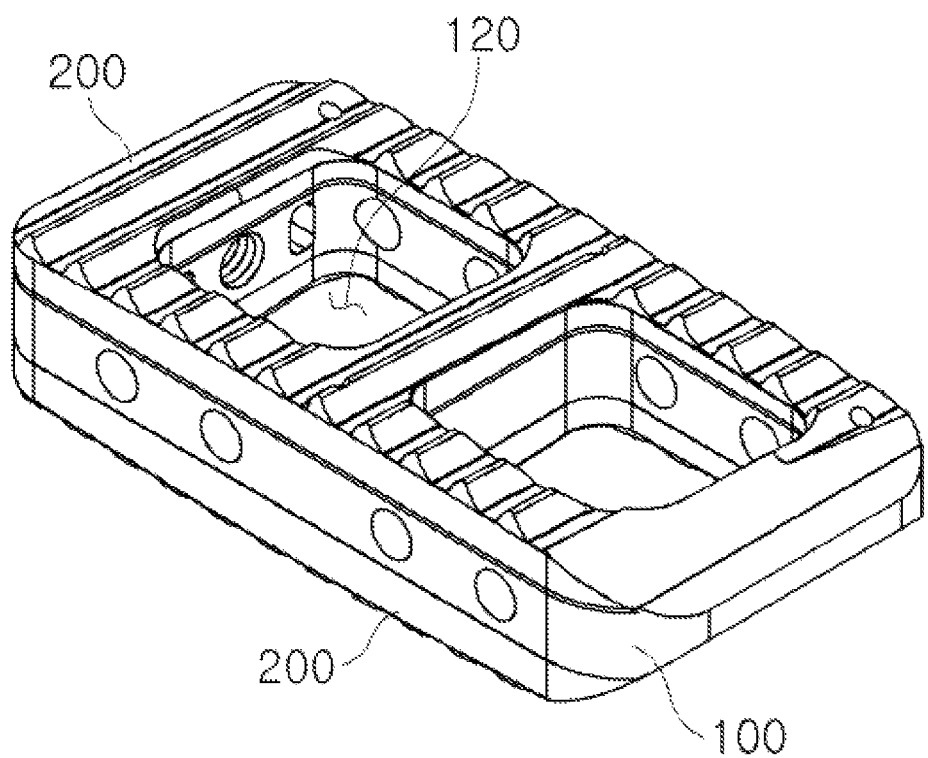
FIG. 14 is a view illustrating various exemplary embodiments of the present invention.

FIGS. 13 and 14 are views illustrating states in which a plurality of hollow portions 120 of the spinal complex cage according to the present invention is arranged perpendicular or parallel to the direction in which the spinal complex cage is inserted between the vertebral bodies.

FIG. 13 illustrates a state in which the three hollow portions 120 are arranged perpendicular to the direction in which the spinal complex cage is inserted between the vertebral bodies. FIG. 14 illustrates a state in which the two hollow portions 120 are arranged parallel to the direction in which the spinal complex cage is inserted between the vertebral bodies. Further, the metal covers 200 and the opening portions 220 formed in the metal covers 200 are formed to correspond to the hollow portions 120.

In the exemplary embodiment, the arrangement pattern of the hollow portions and the number of hollow portions may vary in accordance with the shape of the vertebral body and lesions in consideration of the spinal fusion rate and the rigidity.

Figure 15:
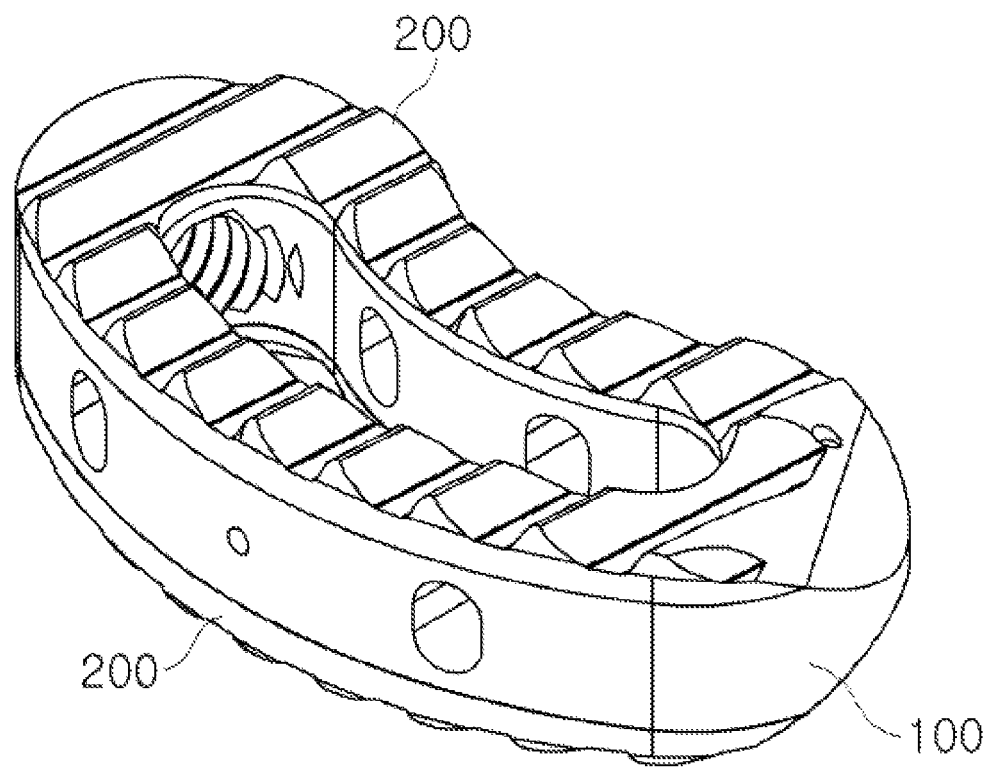
FIG. 15 is a view illustrating various exemplary embodiments of the present invention.
Figure 16:
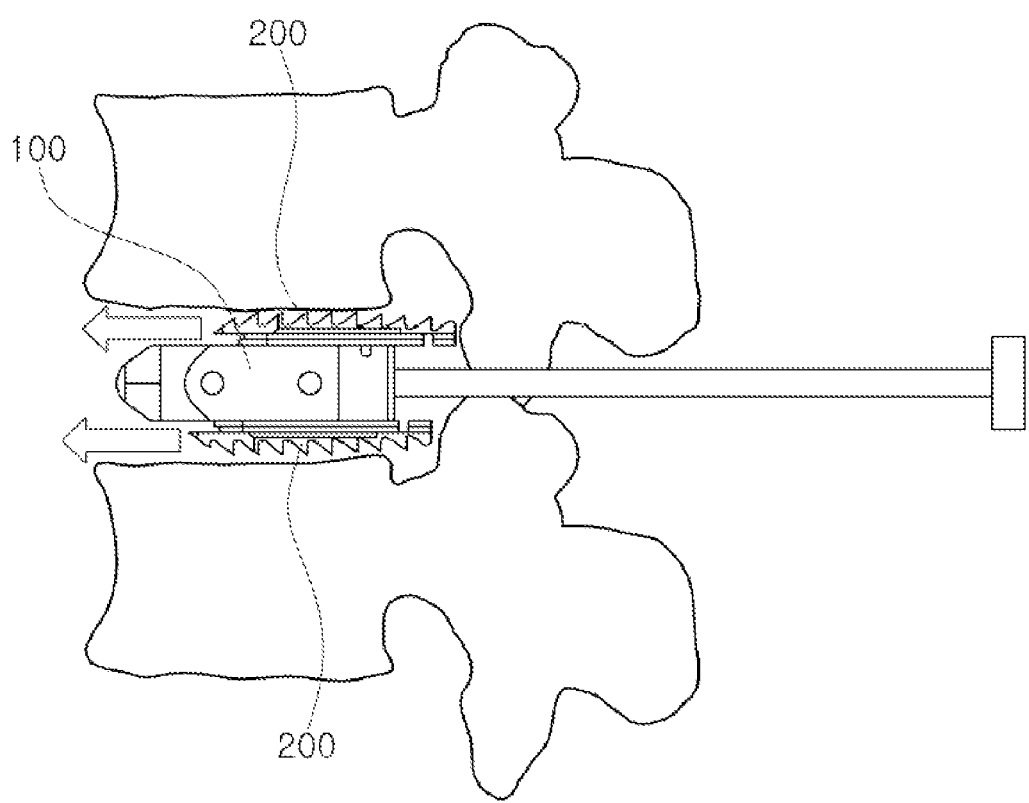
FIG. 16 is a view illustrating a state in which the exemplary embodiment of the present invention is used.

FIG. 15 illustrates a state in which the cage 100, the metal cover 100, the hollow portion, and the opening portion according to the present invention are formed in a curved shape, and the cage 100, the metal cover 100, the hollow portion, and the opening portion may be formed in various shapes in accordance with the shape of the vertebral body and lesions.

FIG. 16 illustrates a state in which the exemplary embodiment of the present invention is used, that is, a state in which the cage 100 is inserted between the vertebral bodies first during surgery (the arrow indicates the direction in which the spinal complex cage is inserted between the vertebral bodies, and the bar at the rear side of the cage is a cage insertion instrument), and then the metal covers 200 are slidingly inserted to naturally expand an interval between the vertebral bodies.

As described above, the present invention relates to a spinal complex cage for an intervertebral body, and more particularly, to a spinal complex cage for an intervertebral body including a cage which is made of a polymeric material, and metal covers which are formed on upper and lower portions of the cage, respectively, such that the spinal complex cage is made of a composite material containing polymers and metal.

In particular, because the cage and the metal cover are detachably coupled to each other, the manufacturing method is simple, and the metal cover is easily coupled to or separated from the cage, such that the spinal complex cage may be variously and quickly applied even during the surgery in accordance with shapes or intervals between the vertebral bodies, thereby enabling the accurate and precise surgical operation.

The metal covers are slidingly coupled to the cage after the cage is inserted, such that an interval between the vertebral bodies is naturally expanded, and as a result, it is possible to easily ensure the interval between the vertebral bodies, thereby making it easy to perform the surgical operation, and enabling the vertebral body to be smoothly and normally restored.

What is claimed is:

1. A spinal complex cage, which includes a cage which is made of a polymeric material, and metal covers which are made of metal and formed on upper and lower portions of the cage, respectively,
    wherein couplers formed on the metal covers are coupled to coupling grooves formed in the cage, such that the metal covers are detachably coupled to the upper and lower portions of the cage,
    wherein each of the metal covers includes:
        an outer cover which is coupled to the cage, has a solid structure, and comprises spikes disposed on an upper surface of the outer cover; and
        an inner cover which is accommodated in and coupled to the outer cover, has a porous structure, and comprises spikes disposed on an upper surface of the inner cover,
    wherein, when the outer cover and the inner cover are coupled to each other, the spikes of the outer cover align with the spikes of the inner cover to form a plurality of parallel combined spikes, and
    wherein, in the inner cover, each of the porous structure, a manufacturing method, a size of a pore, and porosity of the porous structure is configured in accordance with a spinal fusion rate and rigidity of the inner cover.

2. The spinal complex cage of claim 1, wherein a front end portion of the cage is formed in a streamlined shape, and the cage has a hollow portion which vertically penetrates the cage, and a lateral hole portion which communicates with the hollow portion and horizontally penetrates the cage.

3. The spinal complex cage of claim 2, wherein a plurality of hollow portions of the cage is arranged in a horizontal or vertical direction with respect to a direction in which the spinal complex cage is configured to be inserted between intervertebral bodies.

4. The spinal complex cage of claim 2, wherein the metal cover has an opening portion which communicates with the hollow portion.

5. The spinal complex cage of claim 1, wherein each combined spike is formed in the form of a triangular protrusion, and a surface of each combined spike, which is formed in the direction in which the spinal complex cage is configured to be inserted between the intervertebral bodies, is formed to have an angle smaller than 80° with respect to a lower surface of the metal cover.

6. The spinal complex cage of claim 2, wherein the coupling grooves and the couplers are formed such that the metal covers are fitted with the cage in a vertical direction.

7. The spinal complex cage of claim 6, wherein the coupling grooves are configured as horizontal grooves which are horizontally formed in upper and lower surfaces of the cage so as to correspond to a shape of the hollow portion, or vertical grooves which are vertically formed in the upper and lower surfaces of the cage at the periphery of the hollow portion, or the coupling grooves are configured as both of the horizontal grooves and the vertical grooves, and fitting grooves are formed in a lateral direction so as to face an inner surface of the hollow portion of the cage.

* * * * *